(12) United States Patent
Palreddy et al.

(10) Patent No.: US 7,477,935 B2
(45) Date of Patent: Jan. 13, 2009

(54) METHOD AND APPARATUS FOR BEAT ALIGNMENT AND COMPARISON

(75) Inventors: Surekha Palreddy, Maplewood, MN (US); Jay A. Warren, San Juan Capistrano, CA (US); Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 411 days.

(21) Appl. No.: 10/999,274

(22) Filed: Nov. 29, 2004

(65) Prior Publication Data

US 2006/0116725 A1    Jun. 1, 2006

(51) Int. Cl.
*A61B 5/0468* (2006.01)

(52) U.S. Cl. .................. 600/509; 600/510; 600/518; 128/920; 607/14

(58) Field of Classification Search ............ 607/14; 600/509–510, 518; 128/920
See application file for complete search history.

(56) References Cited

U.S. PATENT DOCUMENTS

| | | | |
|---|---|---|---|
| 3,653,387 A | 4/1972 | Ceier | |
| 3,710,374 A | 1/1973 | Kelly | |
| 3,911,925 A | 10/1975 | Tillery, Jr. | |
| 4,030,509 A | 6/1977 | Heilman et al. | |
| 4,157,720 A | 6/1979 | Greatbatch | |
| 4,164,946 A | 8/1979 | Langer | |
| 4,184,493 A | 1/1980 | Langer et al. | |
| 4,191,942 A | 3/1980 | Long | |
| 4,210,149 A | 7/1980 | Heilman et al. | |
| RE30,387 E | 8/1980 | Denniston, III et al. | |
| 4,223,678 A | 9/1980 | Langer et al. | |
| 4,248,237 A | 2/1981 | Kenny | |
| 4,254,775 A | 3/1981 | Langer | |

(Continued)

FOREIGN PATENT DOCUMENTS

DE    298 01 807 U1    7/1998

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner*—Carl H Layno
*Assistant Examiner*—Deborah Malamud
(74) *Attorney, Agent, or Firm*—Pramudji Wendt & Tran, LLP; Ari Pramudji; Mark Schroeder

(57) ABSTRACT

Methods of using a template having a template data set and template parameters to provide improved alignment of captured cardiac signal data to a stored template. More particularly, in an illustrative method, a captured cardiac signal is first configured using template parameters for a stored template. Then, once configured, the captured cardiac signal is then compared to the stored template. Other embodiments include implantable cardiac treatment devices including operational circuitry configured to perform the illustrative method. In a further embodiment, more than one stored templates may be used. Each template can have independently constructed parameters, such that a single captured cardiac signal may be configured using first parameters for comparison to a first template, and using second parameters for comparison to a second template.

10 Claims, 5 Drawing Sheets

U.S. PATENT DOCUMENTS

| | | |
|---|---|---|
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Weilders et al. |
| 4,567,900 A | 2/1986 | Moore |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,439,485 A | 8/1995 | Mar et al. |
| 5,447,521 A | 9/1995 | Anderson et al. |
| 5,476,503 A | 12/1995 | Yang |
| 5,486,199 A | 1/1996 | Kim et al. |
| 5,509,923 A | 4/1996 | Middleman et al. |
| 5,509,928 A | 4/1996 | Acken |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,827,197 A | 10/1998 | Bocek et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,991,657 A | 11/1999 | Kim |
| 6,014,586 A | 1/2000 | Weinberg et al. |
| 6,026,325 A | 2/2000 | Weinberg et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,185,450 B1 | 2/2001 | Seguine et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,334,071 B1 | 12/2001 | Lu |
| 6,345,198 B1 | 2/2002 | Mouchawar et al. |
| 6,411,844 B1 | 6/2002 | Kroll et al. |
| 6,516,225 B1 | 2/2003 | Florio |
| 6,556,860 B1 * | 4/2003 | Groenewegen .............. 600/509 |
| 6,647,292 B1 | 11/2003 | Bardy et al. |
| 6,708,058 B2 | 3/2004 | Kim et al. |
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,865,417 B2 | 3/2005 | Rissmann et al. |
| 6,866,044 B2 | 3/2005 | Bardy et al. |
| 6,889,079 B2 | 5/2005 | Bocek et al. |
| 7,027,856 B2 | 4/2006 | Zhou et al. |
| 7,027,858 B2 | 4/2006 | Cao et al. |
| 7,031,764 B2 | 4/2006 | Schwartz et al. |
| 7,062,315 B2 | 6/2006 | Koyrakh et al. |
| 7,085,599 B2 | 8/2006 | Kim et al. |
| 7,162,301 B2 | 1/2007 | Kim et al. |
| 7,184,815 B2 | 2/2007 | Kim et al. |
| 7,184,818 B2 | 2/2007 | Kim et al. |
| 7,191,004 B2 | 3/2007 | Kim et al. |
| 2001/0027330 A1 | 10/2001 | Sullivan et al. |
| 2002/0183637 A1 | 12/2002 | Kim et al. |
| 2003/0013978 A1 * | 1/2003 | Schlegel et al. ............. 600/509 |
| 2003/0144700 A1 * | 7/2003 | Brown et al. ................. 607/14 |
| 2004/0093035 A1 | 5/2004 | Schwartz et al. |
| 2004/0116972 A1 | 6/2004 | Marcovecchio |
| 2004/0254611 A1 | 12/2004 | Palreddy et al. |
| 2004/0254613 A1 | 12/2004 | Ostroff et al. |
| 2005/0049644 A1 | 3/2005 | Warren et al. |
| 2005/0131476 A1 | 6/2005 | Kim et al. |
| 2005/0131478 A1 | 6/2005 | Kim et al. |

| | | | |
|---|---|---|---|
| 2005/0149125 A1 | 7/2005 | Kim et al. | |
| 2005/0234358 A1 | 10/2005 | Cao et al. | |
| 2005/0234359 A1 | 10/2005 | Cao | |
| 2006/0036288 A1 | 2/2006 | Bocek et al. | |
| 2006/0074331 A1 | 4/2006 | Kim et al. | |
| 2006/0079796 A1 | 4/2006 | Marcovecchio et al. | |
| 2006/0167364 A1 | 7/2006 | Houben | |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 123 716 A2 | 8/2001 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | 1 000 634 A1 | 5/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *PACE*, Jan. 2000, vol. 23, pp. 18-25.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999)vol. 88, No. 8, pp. 559-565.

Tietze U. et al., "Halbleiter-Schaltungstechnik," ©Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

Throne, Robert D. et al., "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 5, Jun. 1991, pp. 561-570.

* cited by examiner

METHOD AND APPARATUS FOR BEAT ALIGNMENT AND COMPARISON

RELATED APPLICATIONS

The present invention is related to U.S. patent application Ser. No. 10/999,853, filed Nov. 29, 2004, now U.S. Pat. No. 7,376,458, and titled METHOD FOR DEFINING SIGNAL TEMPLATES IN IMPLANTABLE CARDIAC DEVICES, the disclosure of which is incorporated herein by reference.

FIELD

The present invention is related to the field of electrical cardiac treatment and devices. More particularly, the present invention is related to analysis of electrical cardiac signals for diagnostic/therapeutic purposes.

BACKGROUND

Implantable cardiac rhythm management devices are an effective treatment in managing irregular cardiac rhythms in particular patients. Implantable cardiac rhythm management devices are capable of recognizing and treating arrhythmias with a variety of therapies. To effectively deliver these therapies, however, cardiac rhythm management devices must first accurately sense and classify an episode.

In order to apply the proper therapy in responding to an episode, some cardiac rhythm management devices compare sensed cardiac signals to a previously stored "template" representing normal sinus rhythm (NSR) or other "template" frequently intended to represent the patient's NSR. Problems arise when the cardiac rhythm management device inaccurately compares a sensed cardiac complex to a stored NSR template, and as a result, misclassifies the sensed cardiac complex. The severity of this problem escalates if the cardiac rhythm management device inappropriately delivers and/or withholds therapy due to the misclassification. In illustration, when a particular group of sensed complexes are erroneously compared to a stored template because of an improper alignment to the template, a cardiac rhythm management device may mistakenly classify these sensed complexes as a mismatch and even possibly as a tachyarrhythmia.

Much of the analysis performed on cardiac signals includes sampling a cardiac signal and comparing the sampled signal to a stored template. Thus, a series of sampled signals are compared to stored data. Often a correlation analysis is performed to compare the two data sets. Typically, a number of peaks will appear in each signal. If the peaks are poorly aligned, low correlation will often result. With poor alignment, a "good" sampled signal may, in analysis, illustrate poor correlation, erroneously indicating treatment. Techniques for enabling and assuring good alignment are therefore desired.

SUMMARY

The present invention, in an illustrative embodiment, makes use of a template having a template data set and template parameters to provide improved alignment of captured cardiac signal data to a stored template. More particularly, in an illustrative method, a captured cardiac signal is first configured using template parameters for a stored template. Then, once configured, the captured cardiac signal is then compared to the stored template. Other embodiments include implantable cardiac treatment devices including operational circuitry configured to perform the illustrative method.

In a further embodiment, more than one stored templates may be used. Each template can have independently constructed templates, such that a single captured cardiac signal may be configured using first parameters for comparison to a first template, and using second parameters for comparison to a second template.

DETAILED DESCRIPTION

The following detailed description should be read with reference to the drawings. The drawings, which are not necessarily to scale, depict illustrative embodiments and are not intended to limit the scope of the invention. Those skilled in the art will recognize that many of the examples provided have suitable alternatives that may be utilized.

The present invention is generally related to implantable cardiac treatment systems that provide therapy for patients who are experiencing particular arrhythmias. The present invention is directed toward detection architectures for use in cardiac rhythm devices. In particular, the present invention is suited for implantable cardiac treatment systems capable of detecting and treating harmful arrhythmias. Although the detection architecture is intended primarily for use in an implantable medical device that provides defibrillation therapy, the invention is also applicable to cardiac rhythm devices (including external devices) directed toward anti-tachyarrhythmia pacing (ATP) therapy, pacing, and other cardiac rhythm devices capable of performing a combination of therapies to treat rhythm disorders.

To date, implantable cardiac treatment systems have been either epicardial systems or transvenous systems. For example, transvenous systems can be implanted generally as shown in FIG. 1B. However, as further explained herein, the present invention is also adapted to function with a subcutaneous implantable cardiac treatment system as shown in FIG. 1A.

Figure 1A:
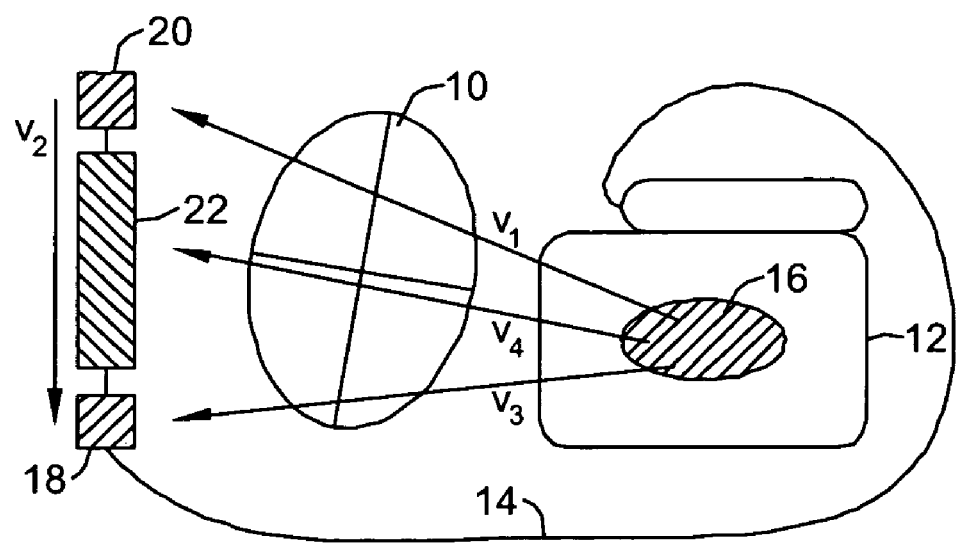
FIGS. 1A-1B illustrate, respectively, representative subcutaneous and intravenous implantable cardiac treatment systems.
Figure 1B:
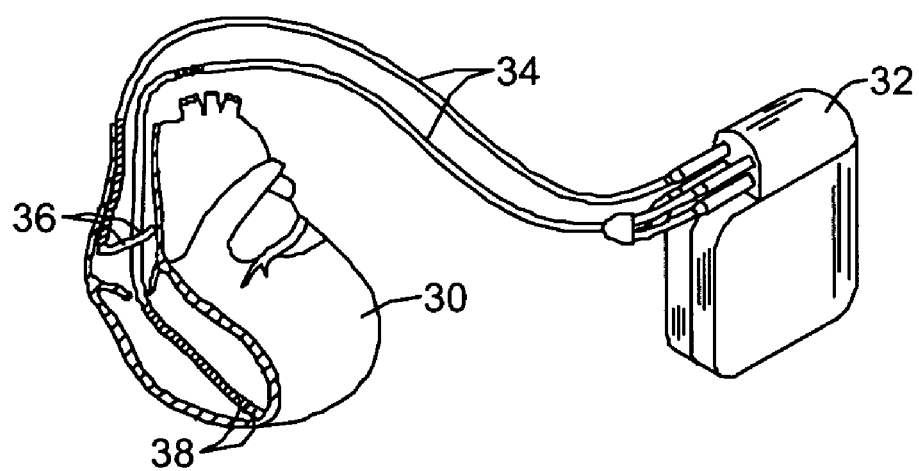

FIG. 1A illustrates a subcutaneously placed implantable cardiac treatment system, in particular, an implantable cardioverter/defibrillator (ICD) system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, in or on the heart muscle, or the patient's vasculature. In some embodiments, a shock is applied using the canister electrode 12 and one of the lead system electrodes 18, 20, or 22, often the coil electrode 22. In other embodiments, one of the sense electrodes 18, 20 may be used in conjunction with the coil electrode 22 for providing a shock.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

Figure 2:
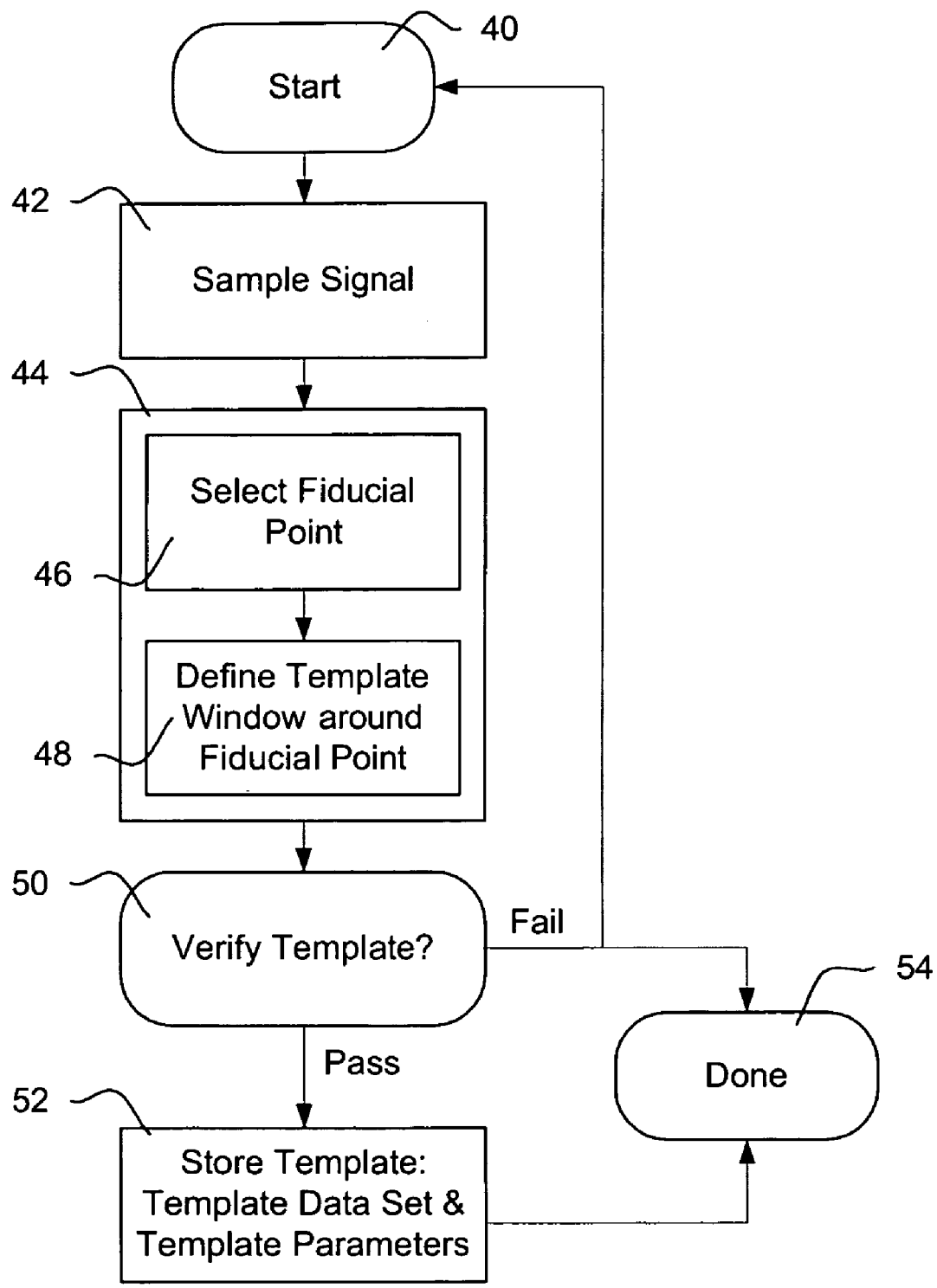
FIG. 2 is a block diagram for an illustrative template formation method.

FIG. 2 is a block diagram for an illustrative template formation method. The illustrative method begins with a start block 40 and has a first step of sampling a signal 42. The signal may be, for example, captured using subcutaneous, transvenous, epicardial, intracardial, or even external electrodes. The illustrative template formation method then defines template parameters 44. Illustratively included in defining the template parameters 44 are the steps of selecting a fiducial point 46 and defining a template window around the fiducial point 48.

With the template parameters defined, and a sample chosen, the next step in the illustrative template formation method is to verify the template 50. This step 50 may include statistical analysis of the template data, comparison of the template to later sampled signals, or other steps that can assure that the template provides an accurate representation of a benign cardiac rhythm. If the template is verified at 50, it passes and is stored as shown at 52. The method of template formation can then be done, as noted at 54. The template is stored both as a template data set and as template parameters. If the template cannot be verified at 50, it fails and the method returns to the start 40. In some embodiments, an attempt to form a template occurs periodically, and if the formation method fails, the method is done 54 until prompted to start again at a later time.

Selecting a fiducial point 46 can be performed in a number of different manners, for example as discussed in U.S. patent application Ser. No. 10/999,851, filed Nov. 29, 2004, now U.S. Pat. No. 7,376,458, and titled METHOD FOR DEFINING SIGNAL TEMPLATES IN IMPLANTABLE CARDIAC DEVICES. For example, a largest positive or negative peak in the signal may be selected. Alternatively, a peak occurring at a particular time (e.g. the first significant peak in the sensed signal) may be selected. In alternative embodiments, a peak or zero in a first or, more likely, second derivative may be selected.

In some methods, the step of setting the template window around the fiducial point 70 is performed by identifying the begin and end of a QRS signal. The observation of monotonic segments may be used to estimate the beginning and end of the QRS segment, as further explained in U.S. patent application Ser. No. 10/999,853, filed Nov. 29, 2004, now U.S. Pat. No. 7,376,458 and titled METHOD FOR DEFINING SIGNAL TEMPLATES IN IMPLANTABLE CARDIAC DEVICES. A monotonic segment is a signal segment of consecutive samples in which the sensed amplitude changes in the same direction or stays the same. For example, a series of consecutive samples in which each successive sample is greater than or equal to (in amplitude) the previous sample would be an increasing monotonic segment. Similarly, a series of consecutive samples in which each successive sample is less than or equal to (in amplitude) the previous sample would be a decreasing monotonic segment. One method for observing monotonic segments is by determining the zero crossing points of the first derivative of the cardiac complex signal. The largest monotonic segment in the sensed signal occurring before the fiducial point may be presumed to represent the start of the QRS complex, while the largest monotonic segment occurring after the fiducial point can then be presumed to represent the end of the QRS complex. One, two, or another number of sample points may be observed beyond these begin and end points for retention in the template window.

For another example, given an isoelectric line in the sensed signal, the number of crossings of the isoelectric line may be noted. Consecutive crossings occurring at intervals of at least a minimum amount may indicate Q-R and R-S intervals, such that the QRS signal can be identified as including the consecutive crossings plus data samples going back and forward a predefined number of samples, such as three samples.

The method shown in FIG. 2 is merely illustrative of one form of template formation. For the present invention, it is sufficient that a tailored template having a template data set and template parameters is or has been formed. Once formed, the template can then be used as further illustrated below.

Figure 3:
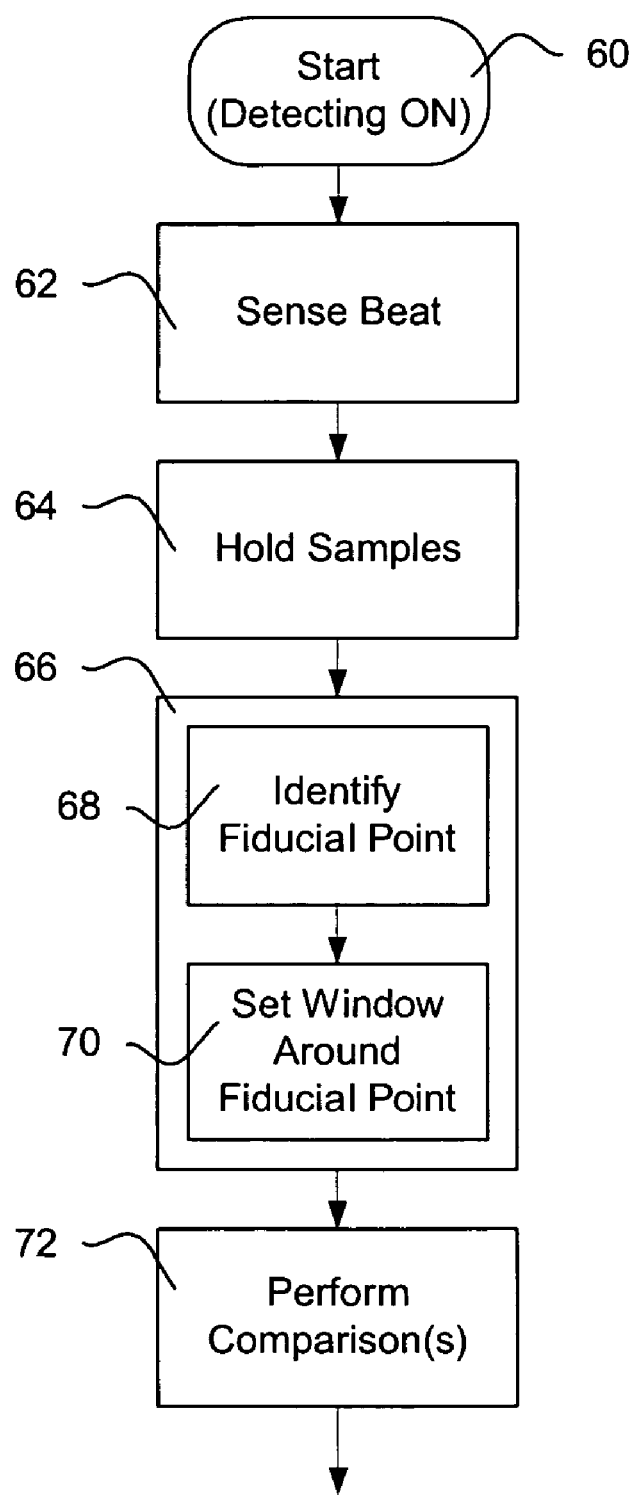
FIG. 3 is a block diagram for an illustrative embodiment.

FIG. 3 is a block diagram for an illustrative embodiment. The method starts 60 with detecting ON such that cardiac signals are being monitored. When a beat (or other event) is sensed, as shown at 62, the method then includes holding a number of samples 64 of the monitored cardiac signal. The beat (or other event) may be sensed in any suitable fashion. If desired, the methods of U.S. patent application Ser. No. 10/858,598, filed Jun. 1, 2004, now U.S. Pat. No. 7,248,598, and titled METHOD AND DEVICES FOR PERFORMING CARDIAC WAVEFORM APPRAISAL, may be used to verify whether the sensed signal likely corresponds to a cardiac event and/or a ventricular event. The disclosure of U.S. patent application Ser. No. 10/858,598 is incorporated herein by reference. If the sensed signal does likely correspond to such an event, the signal may be selected for further analysis.

Next, in accordance with predefined template parameters, the template window is defined at 66. The template window definition may include identifying a fiducial point 68 and setting a window around the fiducial point 70. Next, a comparison is performed 72. The results of the comparison can be used in a variety of manners. Correlation Waveform Analysis is one type of comparison that can be performed. Illustrative types and uses of the comparison are shown in U.S. patent application Ser. No. 10/856,084, filed May 27, 2004, now U.S. Pat No. 7,330,757, and titled METHOD FOR DISCRIMINATING BETWEEN VENTRICULAR AND SUPRAVENTRICULAR ARRHYTHMIAS, the disclosure of which is incorporated herein by reference. Other conventional comparisons and uses thereof may be utilized here as well.

Figure 4A:
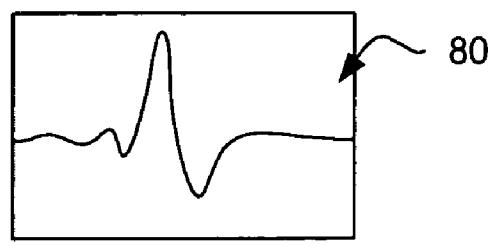
FIGS. 4A-4E show, graphically, an illustrative method for capture, alignment, and comparison of a cardiac signal.
Figure 4B:
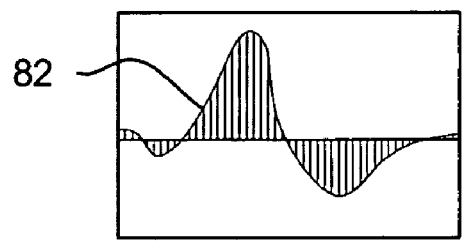
Figure 4C:
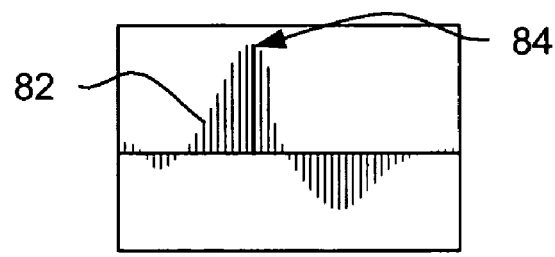
Figure 4D:
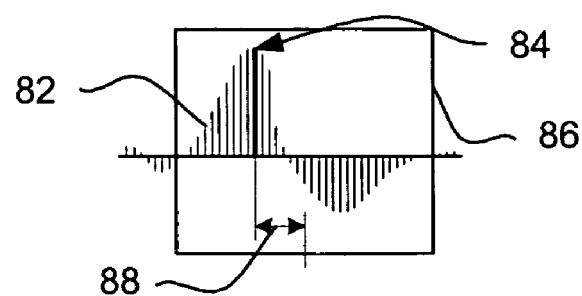

FIGS. 4A-4E show, graphically, an illustrative method for capture, alignment, and comparison of a cardiac signal to a template. FIG. 4A illustrates a sensed signal 80 which can be detected as being a beat. As shown in FIG. 4B, a number of samples 82 are used to discretely capture the beat. FIG. 4C shows that, from the samples 82, a fiducial point 84 has been selected as the peak of the highest positive excursion of the signal from an isoelectric line. FIG. 4D illustrates the windowing of the samples 82, with a window 86 defined around the fiducial point 84. Because the signal has a relatively large trailing portion, the fiducial point 84 is displaced from the center of the window 86 by an offset 88. The steps of selecting a fiducial point and defining the window (as well as the offset) therearound are performed using template parameters defined while forming the template itself.

Figure 4E:
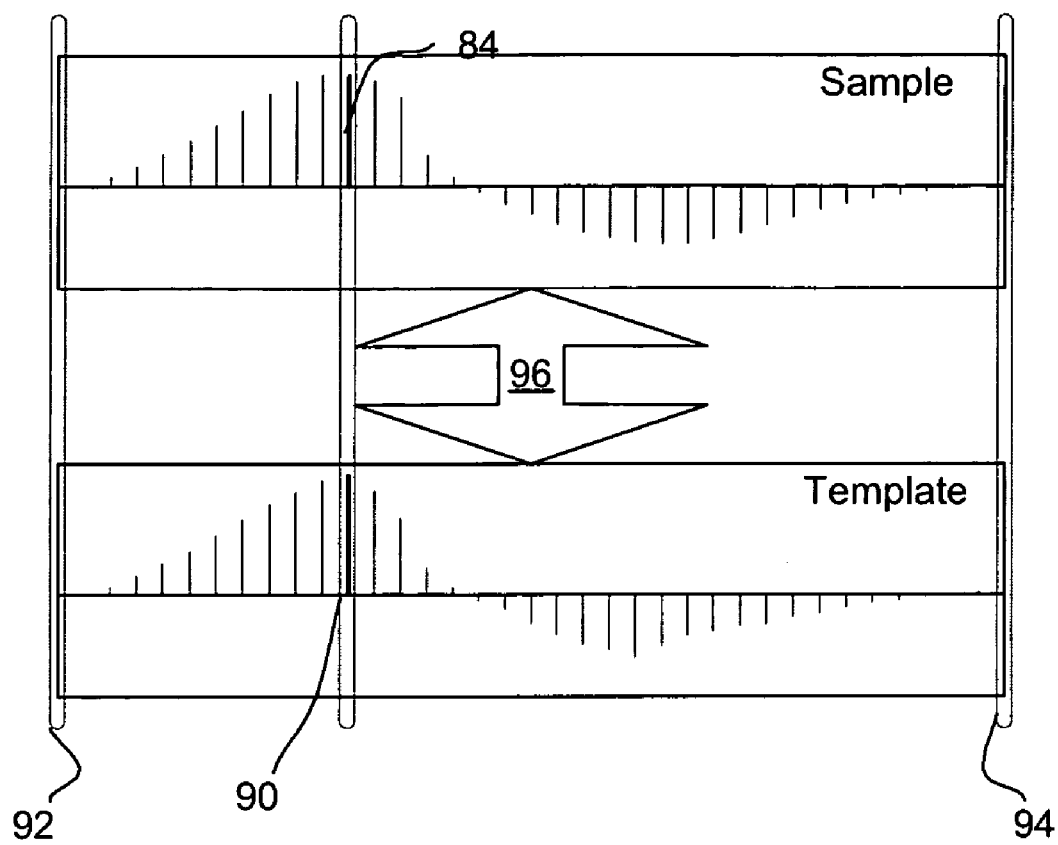

Next, as shown in FIG. 4E, the sample is aligned with the template. More specifically, the sample fiducial point 84 is aligned with the template fiducial point 90. The leading edge 92 and trailing edge 94 of the template and sample windows are then aligned. A comparison 96 can then be performed. By not only aligning the fiducial points 84, 90, but also reconfiguring the sample window and matching the sample window to that used to generate the template, the method advantageously focuses the comparison 96 on the most relevant and useful data available.

The present invention, in some embodiments, is also embodied in devices using operational circuitry including select electrical components provided within the canister 12 (FIG. 1A) or canister 32 (FIG. 1B). In such embodiments, the operational circuitry may be configured to enable the above methods to be performed. In some similar embodiments, the present invention may be embodied in readable instruction sets such as a program encoded in machine or controller readable media, wherein the readable instruction sets are provided to enable the operational circuitry to perform the analysis discussed in the above embodiments. Further embodiments may include a controller or microcontroller adapted to read and execute the above methods. These various embodiments may incorporate the illustrative methods shown in FIGS. 2, 3 and 4A-4E, for example.

The following illustrative embodiments are explained in terms of operational circuitry. The operational circuitry may be configured to include such controllers, microcontrollers, logic devices, memory, and the like, as selected, needed, or desired, for performing the method steps for which each is adapted and configured.

An illustrative embodiment of the present invention includes an implantable cardioverter/defibrillator comprising a lead electrode assembly including a number of electrodes, and a canister housing operational circuitry, wherein the lead electrode assembly is coupled to the canister. In the illustrative embodiment, the operational circuitry is configured to analyze cardiac events using a template having a template data set and template parameters, and the operational circuitry is configured to perform the steps of: capturing a signal using electrodes implanted in a patient's torso; configuring the captured signal in accordance with the template parameters; aligning the template data set with the captured signal; and comparing the template data set to the captured signal.

In a further embodiment, the operational circuitry is further configured to perform the step of classifying the captured signal as being normal or abnormal. In another embodiment, the operational circuitry is configured such that the template parameters include a manner of selecting a fiducial point for the template and the captured signal. In yet another embodiment, the operational circuitry is configured such that the template parameters include a manner of selecting data points around the fiducial point of the captured signal.

In another embodiment, the operational circuitry is further configured such that the template parameters include a manner of selecting data points to form a template window. For another embodiment, the operational circuitry is further configured for performing the step of capturing a signal using subcutaneously implanted electrodes. In yet another embodiment, the operational circuitry is further configured such that: the template includes a fiducial point within the template data set defined by the template parameters; the template data set includes begin and end points relative the fiducial point, the placement of the begin and end points being defined by the template parameters; and the step of configuring the captured signal comprises: selecting a fiducial point in the captured signal; and identifying beginning and ending points of the captured signal according to the placement of the begin and end points of the template data set.

In yet another apparatus embodiment, the operational circuitry is further configured such that the step of comparing the template data set to the captured signal includes performing a correlation waveform analysis between the captured signal defined between its beginning and ending points, and the template data set. The operational circuitry may include a microcontroller. In another embodiment, the operational circuitry includes readable media including an instruction set for performing the capturing, configuring, aligning and comparing steps.

An embodiment of the present invention may include an implantable cardioverter/defibrillator comprising a lead electrode assembly including a number of electrodes, and a canister housing operational circuitry, wherein: the lead electrode assembly is coupled to the canister; the operational circuitry is configured to analyze cardiac events using a template having a template data set and template parameters; and the operational circuitry is configured to perform a number of steps. In the illustrative embodiment, the steps may include, for a number of selected captured cardiac signals, the steps of: configuring the captured signal in accordance with the template parameters, aligning the template data set with the captured signal, and comparing the template data set to the captured signal. The operational circuitry may be further configured for tracking the number of normal and abnormal captured signals, and determining whether therapy is indicated.

In a further embodiment, the operational circuitry is further configured such that the configuring step includes identifying a fiducial point in the selected captured cardiac signals. In another embodiment, the operational circuitry is further configured to perform the steps of: capturing a number of cardiac signals; analyzing the individual captured cardiac signals to determine whether the captured cardiac signals likely represent a cardiac event; and selecting those individual captured cardiac signals which likely represent a cardiac event.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of analyzing cardiac events using a template having a template data set and template parameters, the method comprising:
    capturing a signal using electrodes implanted in a patient's torso;
    configuring the captured signal in accordance with the template parameters, the template parameters including identification of an amplitude peak as a fiducial point and start and end points surrounding the fiducial point;
    aligning the template data set with the configured captured signal using the fiducial point; and
    comparing the aligned template data set to the configured captured signal, including comparing the fiducial point identified in the configured captured signal to the fiducial point of the template data set.

2. The method of claim 1, further comprising;
    if the configured captured signal correlates to the aligned template data set, classifying the captured signal as being normal; or
    if the configured captured signal poorly correlates to the aligned template data set, classifying the captured signal as being abnormal.

3. The method of claim 2, wherein the captured signal, once configured, and if determined to be normal, represents a portion of a single cardiac beat including an R-wave.

4. The method of claim 1, wherein the template parameters include a manner of selecting data points to form a template window.

5. The method of claim 1, wherein the step of capturing a signal is performed using only subcutaneously implanted electrodes.

6. The method of claim 1, wherein the step of comparing the aligned template data set to the configured captured signal includes performing a correlation waveform analysis between the configured captured signal defined between its beginning and ending points, and the aligned template data set.

7. The method of claim 1, wherein the configured captured signal includes a plurality of amplitude samples, and the comparing step includes comparing amplitudes of samples from the configured captured signal to stored amplitudes for the aligned template data set.

8. The method of claim 1, wherein the comparing step includes performing a correlation waveform analysis between the configured captured signal and the aligned template data set.

9. The method of claim 1 wherein:
the template data set comprises a set of i time-ordered samples $\{T0 \ldots Ti\}$ of electrical cardiac signals, with a sample, Tf, of the template data set being identified as a highest amplitude or magnitude signal in the template data set and serving as a fiducial point and with a first set of samples $\{T0 \ldots Tf-1\}$ and a second set of samples $\{Tf+1 \ldots Ti\}$ being identified as belonging to a sample window for the template data set;

the step of configuring the captured signal in accordance with the template parameters comprises identifying a sample within a series of sampled signals as a fiducial point, Sf, that has a highest relative amplitude within a set of such sampled signals, and selecting a set of time-ordered samples around Sf including $\{S0 \ldots Sf-1\}$ and $\{Sf+1 \ldots Si\}$ according to the sample window of the template data set;

the step of aligning the template data set with the captured signal includes aligning time ordered signal samples $\{S0 \ldots Si\}$ with time ordered template samples $\{T0 \ldots Ti\}$ using the fiducial points $\{Sf, Tf\}$; and the step of comparing the aligned template data set to the configured captured signal includes performing correlation analysis of the amplitudes of the aligned data sets $\{S0 \ldots Si\}$ and $\{T0 \ldots Ti\}$.

10. The method of claim 1 wherein:
the template parameters include one or more size parameters indicating how many samples are part of the template, and one or more position parameters indicating a position of a fiducial point in the template; and the step of configuring the captured signal in accordance with the template parameters includes identifying a fiducial point in the captured signal, and defining a signal window around the fiducial point using the one or more size parameters and the one or more position parameters.

* * * * *